(12) United States Patent
Liu et al.

(10) Patent No.: US 8,889,651 B2
(45) Date of Patent: Nov. 18, 2014

(54) TREHALOSE DERIVATIVES, PREPARATION METHOD AND USES THEREOF

(75) Inventors: Zhaopeng Liu, JiNan (CN); Yongli Jiang, JiNan (CN)

(73) Assignee: Joyochem Co., Ltd., Shandong (CN)

( * ) Notice: Subject to any disclaimer, the term of this patent is extended or adjusted under 35 U.S.C. 154(b) by 0 days.

(21) Appl. No.: 13/981,171

(22) PCT Filed: Dec. 30, 2010

(86) PCT No.: PCT/CN2010/002223
§ 371 (c)(1),
(2), (4) Date: Jul. 23, 2013

(87) PCT Pub. No.: WO2012/016367
PCT Pub. Date: Feb. 9, 2012

(65) Prior Publication Data
US 2013/0331346 A1    Dec. 12, 2013

(30) Foreign Application Priority Data
Aug. 6, 2010  (CN) .......................... 2010 1 0246792

(51) Int. Cl.
*C07H 3/04*  (2006.01)
*A61K 31/715*  (2006.01)
*C07H 13/08*  (2006.01)

(52) U.S. Cl.
CPC ..................................... *C07H 13/08* (2013.01)
USPC ........................ 514/53; 536/18.2; 536/123.3

(58) Field of Classification Search
None
See application file for complete search history.

(56) References Cited

FOREIGN PATENT DOCUMENTS

| CN | 101914118 A | 12/2010 |
| WO | WO 2010/050178 | 5/2010 |

OTHER PUBLICATIONS

Igarashi et al., J Nat Prod, 2009, 72, 980-982.*

Igarashi et al., "Brartemicin, an Inhibitor of Tumor Cell Invasion from the Actinomycete *Nonomuraea* sp.," *Journal of Natural Products*, 2009, vol. 72, pp. 980-982.
Boros et al., "Emmyguyacins A and B: Unusual Glycolipids from a Sterile Fungus Species That Inhibit the Low-pH Conformational Change of Hemaggiutinin A during Replication of Influenza Virus," *Journal of Natural Products*, 2002, vol. 65, pp. 108-114.
Gensler et al., "Trehalose Covalently Conjugated to Bovine Serum Albumin," *Journal of Organic Chemistry*, 1977, vol. 42, No. 1, pp. 130-135.
International Search Report issued in International Patent Application No. PCT/CN2010/002223 dated May 19, 2011 (with translation).
Written Opinion issued in International Patent Application No. PCT/CN2010/002223 dated May 19, 2011 (with translation).
International Preliminary Report on Patentability issued in International Patent Application No. PCT/CN2010/002223 dated Nov. 2, 2012 (with translation).

* cited by examiner

*Primary Examiner* — Traviss C McIntosh, III
(74) *Attorney, Agent, or Firm* — Oliff PLC

(57) ABSTRACT

The invention relates to trehalose derivatives with general formula (I), a preparation method and uses thereof, wherein 6,6'-bis(2,3-dimethoxybenzoyl)-α,α-D-trehalose has anti-colon cancer 26-L5 cell invasion activity which is better than that of a natural product Brartemicin, $IC_{50}$ is 0.10 μg/mL (0.15 μM), and when the $IC_{50}$ is 10 μg/mL, 6,6'-bis(2,3-dimethoxybenzoyl)-α,α-D-trehalose has no cytotoxicity, shows high-selectivity anti-tumor invasion activity and can be used for preparing medicaments for preventing and treating invasion and metastasis of colon cancer and the like.

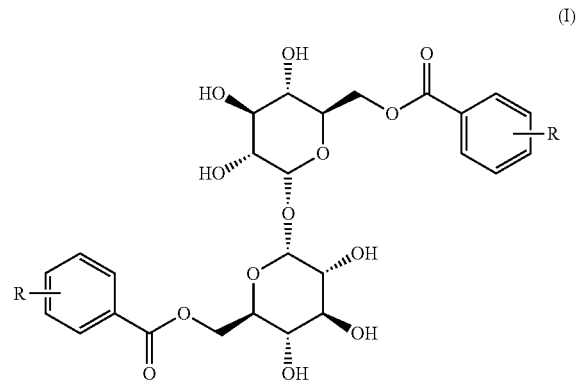

(I)

11 Claims, No Drawings

TREHALOSE DERIVATIVES, PREPARATION METHOD AND USES THEREOF

FIELD OF THE INVENTION

The invention relates to trehalose derivatives, as well as a preparation method, anti-tumor invasion activity and uses thereof, belonging to the technical field of chemistry.

BACKGROUND OF THE INVENTION

Brartemicin is a trehalose derivative separated from a Nonomuraea metabolic product. The compound has strong anti-colon cancer 26-L5 cell invasion activity ($IC_{50}$: 0.39 µM) and has no toxicity against normal cells, thereby being a high-selectivity anti-tumor invasion trehalose derivative.

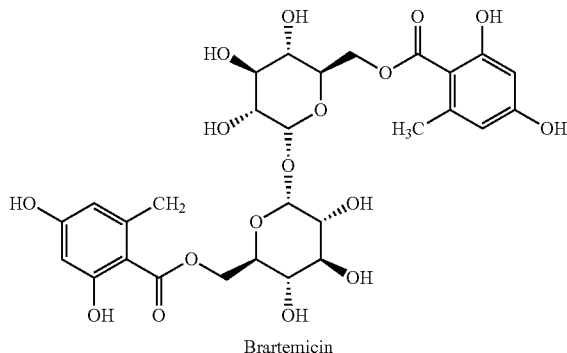

Brartemicin

Tumor invasion means that cells of a malignant tumor leave a primary tumor and attack surrounding tissues, and the mark is that the tumor cells break through a basement membrane. Tumor metastasis means a process that the cells of the malignant tumor deviate from the primary tumor, undergo metastasis to other tissues or organs in various ways to grow continuously and form a secondary tumor which is the same with the nature of the primary tumor. The tumor invasion is a prelude to the tumor metastasis, the tumor metastasis is the continuation and result of the invasion, and the two are closely related. The tumor invasion and metastasis are basic characteristics of malignant tumors, and become the most important reasons causing death of clinical patients with tumors (above 90%), so how to prevent the tumor invasion and metastasis has been the greatest difficulty in tumor treatment. At present, most of anti-tumor medicaments mainly aim at inhibiting the proliferation of the tumor cells and killing the tumor cells, so that they are particularly effective against the tumor cells in a proliferation phase, but invalid against many tumor cells in a dormancy or dormant phase; and in addition, tumor metastasis causes a relatively low cell proliferation ratio and is also insensitive to conventional tumor chemotherapy. Therefore, the development of the anti-tumor invasion and metastasis medicaments against the metastasis process and micrometastases becomes particularly important.

SUMMARY OF THE INVENTION

Against the deficiencies of the prior art, the invention provides α,α-D-trehalose-6,6'-diaryl ester derivatives and preparation methods thereof. The invention further provides activity experiment results and uses of the compounds. Based on the principles of similarity and diversity of molecular design, in the invention designed and synthesized are a series of α,α-D-trehalose-6,6'-diaryl ester derivatives, the anti-tumor invasion activity of which is researched, and it is found that part of trehalose derivatives have strong anti-tumor invasion activity and high selectivity and thus have potential anti-tumor invasion and metastasis application value.

Explanation of Terms

Mitsunobu reaction: a bimolecular nucleophilic substitution reaction invented by Japanese scientist Mitsunobu, O. Through the reaction, alcohols can be transformed to a variety of compounds, such as esters and the like through the reaction with triphenylphosphine and diethyl azodicarboxylate (DEAD).

DCC: N,N'-dicyclohexylcarbodiimide.

EDC: 1-(3-dimethylaminopropyl)-3-ethylcarbodiimide hydrochloride.

DMAP: 4-N,N-dimethyl pyridine.

HOBt: 1-hydroxy-benzo-triazole.

The technical solution of the invention is as follows:

Trehalose derivatives have the structures with general formula (I):

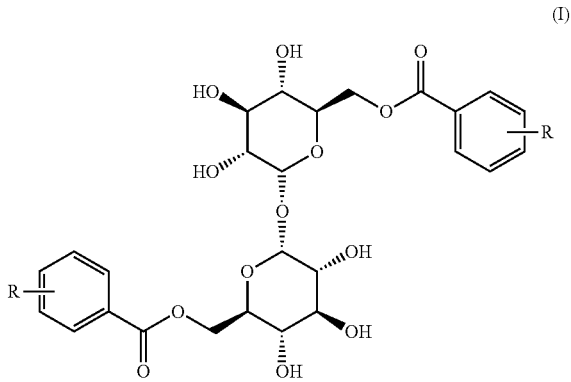

(I)

wherein R represents substituents in different positions of a benzene ring, including mono-substitution, bis-substitution or tri-substitution; and R group substituents are methoxy, hydroxy, amino, alkyl, halogen, nitro or benzyloxy.

Preferably, R in general formula (I) is 2,3-dimethoxy, 2-methoxy, 4-hydroxy, 2,6-difluoro or 2-methyl-6-amino; and R can be the same or different during bis-substitution or tri-substitution.

Preferably, the compound (I) is one of the following components:

6,6'-bis(2-methoxybenzoyl)-α,α-D-trehalose (3a), 6,6"-bis(2-methylbenzoyl)-α,α-D-trehalose (3b), 6,6'-bis(4-methoxybenzoyl)-α,α-D-trehalose (3c), 6,6'-bis(4-hydroxybenzoyl))-α,α-D-trehalose (3d), 6,6'-bis(2,3-dimethoxybenzoyl))-α,α-D-trehalose (3e), 6,6'-bis(2,6-difluorobenzoyl))-α,α-D-trehalose (3f), 6,6'-bis(2-methyl-6-aminobenzoyl))-α,α-D-trehalose (3g), 6,6'-his(3-methoxy-4-fluorobenzoyl))-α,α-D-trehalose (3h) or 6,6'-bis(3,4,5-trimethoxybenzoyl))-α,α-D-trehalose (3i).

The synthetic route of a preparation method of the trehalose derivatives disclosed by the invention is as follows:

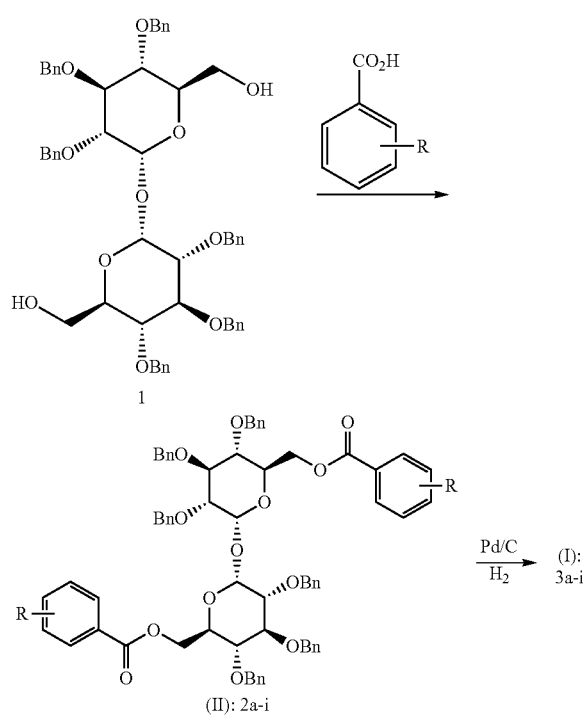

In the abovementioned reaction formula, the groups represented by R are the same as previously described, and the structures of the compounds represented by (I) are the same as previously described.

According to the synthetic route, the trehalose derivative 1 protected by benzyl is taken as a raw material to prepare an intermediate (II) by condensation with different substituted benzoic acids; and benzyl protection is finally removed by catalytic hydrogenation to get the trehalose derivatives (I).

The intermediate (II) can be prepared by adopting conventional reaction of acyl chlorides and alcohols, namely the different substituted benzoic acids are reacted with thionyl chloride, phosphorus pentachloride, phosphorus trichloride or oxalyl chloride to prepare the acyl chlorides, and then the reaction with the compound 1 is further preformed in the presence of an alkali, but the yield is lower (0-60%). A DCC or EDC condensation agent can also be utilized for performing direct condensation in the presence of DMAP or HOBt, but the yield is lower (0-40%). Studies find that, by adopting Mitsunobu reaction, the intermediate (II) can be prepared with high yield.

The specific steps of the preparation method of the trehalose derivatives disclosed by the invention are as follows:

(1) dissolving one equivalent of 2,2',3,3',4,4'-hexabenzyloxy)-α,α-D-trehalose (compound 1) in an appropriate solvent, adding 3.0 equivalents of substituted benzoic acid and 4.0 equivalents of triphenylphosphine, dropwise adding 2.0 equivalents of Mitsunobu reagent, performing reaction under stirring for 2-12 hours, separating and purifying to get the intermediate compound (II); and (2) dissolving the intermediate compound (II) in a certain amount of solvent, adding a palladium/carbon catalyst, reducing under hydrogen flow and purifying to obtain the trehalose derivatives (I).

Preferably, substituted benzoic acid in step (1) is 2-methoxybenzoic acid, o-methylbenzoic acid, 4-methoxybenzoic acid, 4-benzyloxybenzoic acid, 2,3-dimethoxybenzoic acid, 2,6-difluorobenzoic acid, 2-methyl-6-nitrobenzoic acid, 3-methoxy-4-fluorobenzoic acid or 3,4,5-trimethoxybenzoic acid.

Preferably, the solvent in step (1) is tetrahydrofuran or methylene dichloride, preferably tetrahydrofuran.

Preferably, the Mitsunobu reagent in step (1) is diisopropyl azodicarboxylate (DIAD) or diethyl azodicarboxylate (DEAD), preferably diisopropyl azodicarboxylate.

Preferably, the reaction temperature in step (1) is 0° C.-25° C.

Preferably, the solvent in step (2) is an ethyl acetate-ethanol mixed solution in the volume ratio of 1:1; and the catalyst is 10% palladium/carbon.

Pharmaceutical Composition Containing Trehalose Derivatives Disclosed by the Invention A pharmaceutical composition comprises the trehalose derivatives of the invention and one or more pharmaceutically acceptable carriers or excipients.

Uses of Trehalose Derivatives Disclosed by the Invention

The trehalose derivatives described in the invention can be used for preparing anti-tumor invasion and metastasis medicaments and can be specifically used for preparing the medicaments against colon cancer 26-L5 cell invasion and metastasis.

Anti-tumor Invasion Activity Experiment of Trehalose Derivatives (1) Experimental principle:
Invasion and metastasis are basic characteristics of malignant tumors. During the tumor metastasis process, the tumor cell invasion into a basement membrane is an important link. A conventional recombinant basement membrane invasion experiment is adopted, a natural product Brartemicin is taken as positive control, and the inhibition action of trehalose derivatives against colon cancer 26-L5 cell invasion activity is determined.

(2) Experimental materials:
Polycarbonate membrane 8 μm (Nucleopore, Pleasanton, Calif., USA); Transwell cell culture chamber (Costar 3422, Cambridge, Mass., USA); fibronectin (FN; Collaborative Research Inc., Bedford, Mass., USA); Matrigel (Collaborative Research Inc., Bedford, Mass., USA); RPMI1640 culture medium containing 1% of fetal calf serum (FCS) (Collaborative Research Inc., Bedford, Mass., USA); and hematoxylin-eosin (HE) staining kit (Collaborative Research Inc., Bedford, Mass, USA).

(3) Experimental method:
20 μg of fibronectin is smeared on the lower layer of a Transwell cell culture chamber, and 5 μg of Matrigel is smeared on the upper layer. Colon cancer 26-L5 cells in an exponential growth phase are suspended in an RPMI1640 culture medium containing 1% of fetal calf serum (FCS), which contains different concentrations of the trehalose derivatives or different concentrations of Brartemicin. 100 μl of the abovementioned suspension ($2 \times 10^4$ cells/chamber) is taken and added into the upper layer of the chamber, and further immersed in a complete culture solution of a 24-well plate, incubation is performed in an incubator containing 5% of $CO_2$ at the temperature of 37° C. for 6-8 hours, then the chamber is taken out, filter membranes are fixed through methanol, HE staining is performed for 3 min, and the cells which do not penetrate the upper layers of the membranes are wiped off by a cotton swab after the end of staining. The filter ester membranes contain the colored colon cancer 26-L5 cells after invasion. The ester membranes are placed on glass slides and are subjected to permeabilization by xylene, neutral resin is used for sealing, and the invasion cells are counted under a 400× microscope. The number of the penetrating cells of each membrane is counted from five different visual fields, namely upper, lower, left, right and middle visual fields, the average value is calculated, and three filter membranes are arranged in parallel in each group.

(4) Experiment results:

The natural product Brartemicin is taken as the positive control, the inhibition action of the trehalose derivatives against the colon cancer 26-L5 cell invasion activity is determined, and the activity experiment results are as shown in the following Table 1.

TABLE 1

| Compounds | R | $IC_{50}$ (μg/mL) |
|---|---|---|
| Brartemicin |  | 0.25 |
| 3a | 2-OMe | 1.00 |
| 3b | 2-Me | NA |
| 3c | 4-OMe | NA |
| 3d | 4-OH | 1.00 |
| 3e | 2,3-(OMe)$_2$ | 0.10 |
| 3f | 2,6-F$_2$ | 1.00 |
| 3g | 2-CH$_3$,6-NH$_2$ | 1.00 |
| 3h | 3-OMe,4-F | NA |
| 3i | 3,4,5-(OMe)$_3$ | NA |

NA: no activity when IC50 is 10 μg/mL

What is noteworthy is that all the tested compounds have no cytotoxicity when the concentration is 10 μg/mL and the compounds 3a, 3d, 3e, 3f and 3g show strong anti-colon cancer 26-L5 cell invasion activity; and particularly, the compound 3e, when $IC_{50}$ is 0.10 μg/mL (0.15 μM), has the stronger activity than the natural product Brartemicin, and thus has the potential of being further developed into anti-tumor invasion and metastasis medicaments and the potential application value in the treatment of colon cancer.

In summary, the trehalose derivatives disclosed by the invention, in particular the compound 3e, have strong anti-colon cancer 26-L5 cell invasion activity and can be put into use as anti-tumor invasion and metastasis lead compounds or medicaments, and specifically, the trehalose derivatives can be used as tumor invasion and metastasis inhibitors for preparing anti-tumor medicaments; or the trehalose derivatives can be used as formula medicaments together with other anti-tumor medicaments so as to prevent the metastasis of the colon cancer, treat the colon cancer and the like.

DETAILED DESCRIPTION OF THE EMBODIMENTS

In order to describe the invention in more detail, the following preparation examples are provided. However, the scope of the invention is not limited to these examples. In embodiment 2, 10% palladium/carbon refers to the percentage by weight of palladium in the catalyst palladium/carbon.

Embodiment 1: Preparation of Intermediate Compound (II)

2,2',3,3',4,4'-hexabenzyloxy-α,α-D-trehalose (300 mg, 0.34 mmol) is dissolved in 10 ml of dry tetrahydrofuran (THF), the mixture is cooled to 0° C., 2-methoxybenzoic acid (155 mg, 1.02 mmol), triphenylphosphine (300 mg, 1.33 mmol) and diisopropyl azodicarboxylate (300 μl, 0.68 mmol) are sequentially added in the condition of nitrogen protection, and reaction is performed under stirring for 2 hours. 10 ml of ice water is added and extraction is performed by using ethyl acetate. Silica gel column chromatography (petroleum ether/ethyl acetate is 15-3:1) is performed to get 324 mg of 6,6'-bis (2-methoxybenzoyl)-2,2',3,3',4,4')-α,α-D-trehalose 2a, wherein the yield is 82.8%. 2b-2i are prepared by the same method, and the difference is that the added substituted benzoic acids are o-methylbenzoic acid, 4-methoxybenzoic acid, 4-benzyloxybenzoic acid, 2,3-dimethoxybenzoic acid, 2,6-difluorobenzoic acid, 2-methyl-6-nitrobenzoic acid, 3-methoxy-4-fluorobenzoic acid or 3,4,5-trimethoxybenzoic acid sequentially.

308 mg of 6,6'-bis(2-methylbenzoyl)-2,2',3,3',4,4'-hexabenzyloxy)-α,α-D-trehalose 2b is obtained, and the yield is 81.0%.

320 mg of 6,6'-bis(4-methoxybenzoyl)-2,2',3,3',4,4'-hexabenzyloxy)-α,α-D-trehalose 2c is obtained, and the yield is 81.8%.

301 mg of 6,6'-bis(4-benzyloxy-benzoyl)-2,2,3,3',4,4'-hexabenzyloxy)-α,α-D-trehalose 2d is obtained, and the yield is 68.0%.

280 mg of 6,6'-bis(2,3-dimethoxybenzoyl)-2,2',3,3',4,4'-hexabenzyloxy)-α,α-D-trehalose 2e is obtained, and the yield is 68.0%.

328 mg of 6,6'-bis(2,6-difluorobenzoyl)-2,2',3,3',4,4'-hexabenzyloxy)-α,α-D-trehalose 2f is obtained, and the yield is 83.0%.

315 mg of 6,6'-bis(2-methyl-6-nitrobenzoyl)-2,2',3,3',4,4'-hexabenzyloxy)-α,α-D-trehalose 2g is obtained, and the yield is 76.7%.

315 mg of 6,6'-bis(3-methoxy-4-fluorobenzoyl)-2,2',3,3',4,4'-hexabenzyloxy)-α,α-D-trehalose 2h is obtained, and the yield is 68.0%.

280 mg of 6,6'-bis(3,4,5-trimethoxybenzoyl)-2,2',3,3',4,4'-hexabenzyloxy)-α,α-D-trehalose 2l is obtained, and the yield is 68.8%.

Embodiment 2: Preparation of Trehalose Derivatives (I)

6,6'-bis(2-methoxybenzoyl)-2,2',3,3',4,4'-hexabenzyloxy)-α,α-D-trehalose 2a (190 mg, 0.165 mmol) is dissolved in 5 ml of anhydrous ethanol-ethyl acetate (1:1), 120 mg of 10% Pd/C is added and reaction is performed under stirring at a certain hydrogen pressure for 24 hours. Filtering is performed and then organic liquid is concentrated. Silica gel column chromatography (dichloromethane/methanol is 15-6:1) is performed to get 70 mg of 6,6'-bis(2-methoxybenzoyl))-α,α-D-trehalose 3a, wherein the yield is 66.8%. ESI-MS m/z is 633.4 (M+Na)$^+$.

3b-3i are prepared from the intermediates 2b-2i by the same method.

6,6'-bis(2-methylbenzoyl))-α,α-D-trehalose 3b is obtained, and the yield is 63.3%. ESI-MS m/z is 610.4 (M+Na)$^+$.

6,6'-bis(4-methoxybenzoyl))-α,α-D-trehalose 3c is obtained, and the yield is 69.5%. ESI-MS m/z is 633.4 (M+Na)$^+$.

6, 6'-bis(4-hydroxybenzoyl))-α,α-D-trehalose 3d is obtained, and the yield is 64.7%. ESI-MS m/z is 605.3 (M+Na)$^+$.

6,6'-bis(2,3-dimethoxybenzoyl))-α,α-D-trehalose 3e is obtained, and the yield is 60.2%. ESI-MS m/z is 693.4 (M+Na)$^+$.

6,6'-bis(2,6-difluorobenzoyl))-α,α-D-trehalose 3f is obtained, and the yield is 66.3%. ESI-MS m/z is 645.3 (M+Na)$^+$.

6,6'-bis(2-methyl-6-aminobenzoyl))-α,α-D-trehalose 3g is obtained, and the yield is 35.8%. ESI-MS m/z is 631.3 (M+Na)$^+$.

6,6'-bis(3-methoxy-4-fluorobenzoyl))-α,α-D-trehalose 3b is obtained, and the yield is 82.2%. ESI-MS m/z is 669.3 (M+Na)+.

6, 6'-bis(3, 4, 5-trimethoxybenzoyl))-α,α-D-trehalose 3l is obtained, and the yield is 58.7%. ESI-MS m/z 753.5 (M+Na)+.

The invention claimed is:

1. Trehalose derivatives with general formula (I):

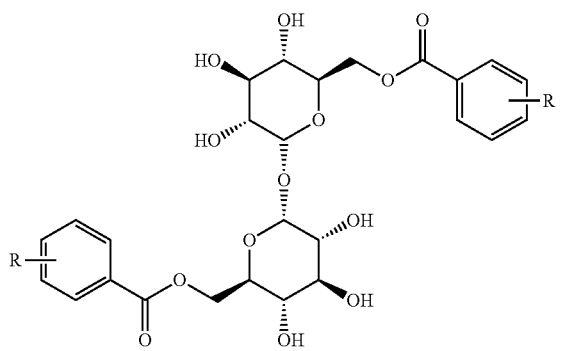

(I)

wherein
R represents a methoxy group or a halogen group, which is a substituent in at least one position of each benzene ring, and
each benzene ring is substituted with 1, 2 or 3 R groups.

2. The trehalose derivatives according to claim 1, wherein the trehalose derivatives include one of the following compounds:
6,6'-bis(2-methoxybenzoyl)-α,α-D-trehalose (3a),
6,6'-bis(4-methoxybenzoyl)-α,α-D-trehalose (3c),
6,6'-bis(2,3-dimethoxybenzoyl) -α,α-D-trehalose (3e),
6,6'-bis(2,6-difluorobenzoyl)-α,α-D-trehalose (3f),
6,6'-bis(3-methoxy-4-fluorobenzoyl)-α,α-D-trehalose (3h) or
6,6'-bis(3,4,5-trimethoxybenzoyl)-α,α-D-trehalose (3i).

3. A preparation method of the trehalose derivatives according to claim 1, comprising the following steps:
the synthetic route

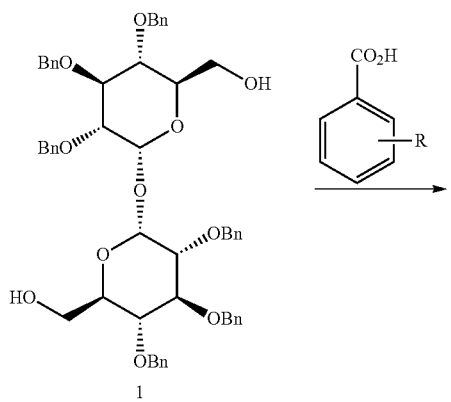

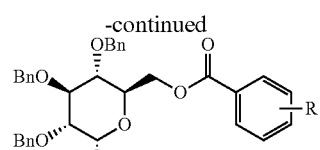

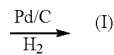

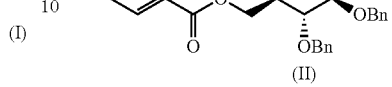

(II)

comprising the following specific operation steps:
(1) dissolving one equivalent of 2,2',3,3',4,4'-hexabenzyloxy-α,α-D-trehalose (compound (1) in an appropriate solvent, adding 3.0 equivalents of substituted benzoic acid and 4.0 equivalents of triphenylphosphine, dropwise adding 2.0 equivalents of Mitsunobu reagent, performing reaction under stirring for 2-12 hours, separating and purifying to get an intermediate compound (II); and
(2) dissolving the intermediate compound (II) in a certain amount of solvent, adding a palladium/carbon catalyst, reducing under hydrogen flow, and purifying to obtain the trehalose derivatives of general formula (I).

4. The preparation method of the trehalose derivatives according to claim 3, wherein the substituted benzoic acid in step (1) is 2-methoxybenzoic acid, 4-methoxybenzoic acid, 2,3-dimethoxvbenzoic acid, 2,6-difluorobenzoic acid, 3-methoxy-4-fluorobenzoic acid or 3,4,5-trimethoxybenzoic acid.

5. The preparation method of the trehalose derivatives according to claim 3, wherein the solvent in step (1) is tetrahydrofuran or methylene dichloride.

6. The preparation method of the trehalose derivatives according to claim 3, wherein the Mitsunobu reagent in step (1) is diisopropyl azodicarboxylate (DIAD).

7. The preparation method of the trehalose derivatives according to claim 3, wherein the solvent in step (2) is an ethyl acetate-ethanol mixed solution in the volume ratio of 1:1, and the catalyst is 10% palladium/carbon.

8. A pharmaceutical composition against colon cancer 26-L5 cell invasion and metastasis, comprising the trehalose derivatives according to claim 1 and one or more pharmaceutically acceptable carriers or excipients.

9. A method of preparing medicaments against colon cancer 26-L5 cell invasion and metastasis including adding the trehalose derivatives according to claim 1 to the medicaments.

10. A method of preparing medicaments against colon cancer 26-L5 cell invasion and metastasis including adding the trehalose derivatives according to claim 2 to the medicaments.

11. A pharmaceutical composition against colon cancer 26-L5 cell invasion and metastasis, comprising the trehalose derivatives according to claim 2 and one or more pharmaceutically acceptable carriers or excipients.

* * * * *